United States Patent
Trayanova et al.

(10) Patent No.: US 12,268,451 B2
(45) Date of Patent: *Apr. 8, 2025

(54) PERSONALIZED COMPUTATIONAL MODELING OF ATRIAL FIBROSIS TO GUIDE CATHETER ABLATION OF ATRIAL FIBRILLATION

(71) Applicant: THE JOHNS HOPKINS UNIVERSITY, Baltimore, MD (US)

(72) Inventors: Natalia A. Trayanova, Baltimore, MD (US); Kathleen McDowell, Baltimore, MD (US)

(73) Assignee: THE JOHNS HOPKINS UNIVERSITY, Baltimore, MD (US)

(*) Notice: Subject to any disclaimer, the term of this patent is extended or adjusted under 35 U.S.C. 154(b) by 0 days.

This patent is subject to a terminal disclaimer.

(21) Appl. No.: 18/480,049

(22) Filed: Oct. 3, 2023

(65) Prior Publication Data
US 2024/0024031 A1    Jan. 25, 2024

Related U.S. Application Data

(63) Continuation of application No. 17/076,091, filed on Oct. 21, 2020, now Pat. No. 11,793,573, which is a
(Continued)

(51) Int. Cl.
*A61B 34/10* (2016.01)
*A61B 18/00* (2006.01)

(52) U.S. Cl.
CPC .... *A61B 34/10* (2016.02); *A61B 2018/00351* (2013.01); *A61B 2034/101* (2016.02); *A61B 2034/104* (2016.02); *A61B 2034/105* (2016.02)

(58) Field of Classification Search
CPC .... A61B 2018/00351; A61B 2034/101; A61B 2034/104; A61B 2034/105; A61B 34/10
See application file for complete search history.

(56) References Cited

U.S. PATENT DOCUMENTS

| 7,681,579 B2 | 3/2010 | Schwartz |
| 2011/0224962 A1 | 9/2011 | Goldberger et al. |

(Continued)

FOREIGN PATENT DOCUMENTS

| CN | 102831289 A | 12/2012 |
| KR | 20120056037 A | 6/2012 |

(Continued)

OTHER PUBLICATIONS

Akoum et al., Atrial fibrosis helps select the appropriate patient and strategy in catheter ablation of atrial fibrillation: A DE-MRI guided approach. J Cardiovasc Electrophysiol. 2011; 22; 16-22.

(Continued)

*Primary Examiner* — Katherine L Fernandez
(74) *Attorney, Agent, or Firm* — MH2 Technology Law Group LLP

(57) ABSTRACT

Methods, system, and media for identifying one or more ablation locations in an atrial tissue region in an atrial fibrillation (AF) patient with atrial fibrosis are disclosed. Three-dimensional imaging data representing the atria of the patient may be received. A patient-specific model of the atria may be generated from the three-dimensional imaging data. Simulation of the AF on the patient-specific model may be conducted to identify AF-perpetrating regions. One or more ablation locations in the atria may be identified from the AF-perpetrating regions.

13 Claims, 5 Drawing Sheets
(4 of 5 Drawing Sheet(s) Filed in Color)

Related U.S. Application Data continuation of application No. 15/814,053, filed on Nov. 15, 2017, now Pat. No. 10,813,698, which is a continuation of application No. 14/094,334, filed on Dec. 2, 2013, now abandoned.

(56) References Cited

U.S. PATENT DOCUMENTS

| | | |
|---|---|---|
| 2012/0232417 A1 | 9/2012 | Zhang |
| 2013/0211436 A1 | 8/2013 | Larson et al. |
| 2014/0088395 A1 | 3/2014 | Bubois |

FOREIGN PATENT DOCUMENTS

| | | |
|---|---|---|
| WO | 2012021022 A1 | 2/2012 |
| WO | 2012109618 A2 | 8/2012 |

OTHER PUBLICATIONS

Atienza et al., Real-time dominant frequency mapping and ablation of dominant frequency sites in atrial fibrillation with left-to-right frequency gradients predicts long-term maintenance of sinus rhythm. Heart Rhythm. 2009; 6:33-40.

Byrd et al., Importance of geometry and refractory period in sustaining atrial fibrillation: Testing the critical mass hypothesis. Circulation. 2005; 112:17-13.

Camelliti et al., Fibroblast network in rabbit sinoatrial node: Structural and functional identification of homogeneous and heterogeneous cell coupling. Circ Res. 2004; 94:828-835.

Cappato et al., Updated worldwide survey on the methods, efficacy, and safety of catheter ablation for human atrial fibrillation. CircArrhythm Electrophysiol. 2010v332-38.

Courtemanche et al., Ionic targets for drug therapy and atrial fibrillation-induced electrical remodeling: Insights from a mathematical model. Cardiovasc Res. 1999; 42:477-489.

Daccarett et al., MRI of the left atrium: Predicting clinical outcomes inpatients with atrial fibrillation. Expert review of cardiovascular therapy. 2011; 9:105-111.

Du et al., Trpm7-mediated cat+ signals confer fibrogenesis in human atrial fibrillation. Circ Res. 2010; 106:992-1Q03.

Feinberg et al., Prevalence, age distribution, and gender of patients with atrial fibrillation. Analysis and implications. Arch Intern Med. 1995; 155:469-473.

Haissaguerre et al., Electrophysiological end point for catheter ablation of atrial fibrillation initiated from multiple pulmonary venous foci. Circulation. 2000; 101.1409-1417.

Haissaguerre et al., Spontaneous initiation of atrialfibrillation by ectopic beats originating in the pulmonary veins. N Engl J Med. 1998; 339:659-666.

Hanson et al., Right atrial free wall conduction velocity and degree of anisotropy in patients with stable sinus rhythm studied during open heart surgery. Eur HeartJ. 1998; 19:293-300.

Kneller et al., Cholinergic atrial fibrillation in a computer model of a two-dimensional sheet of canine atrial cells with realistic ionic properties. Circulation Research. 2002; 90:E73-E87.

Kostin et al., Structural correlate of atrial fibrillation in human patients. Cardiovasc Res. 2Q02; 54:361-379.

Krueger et al., Patient-specific modeling of atrial fibrillation initiation: Clinical and computational studies of repolarization restitution and activation latency. CircArrhythm Electrophysiol. 2012;5.1149-1159.

Krummen et al., Mechanisms of human atrial fibrillation initiation: Clinical and computational studies of repolarization restitution and activation latency. CircArrhythm Electrophysiol. 2012; 5.1149-1159.

Kuo et al., Characteristics and possible mechanism of ventricular arrhythmia dependent on the dispersion of action potential durations. Circulation. 1983; 67:1356-1367.

Kwon et al., "A patent-specific model of cirtual ablation for atrial fibrillation", Engineering in Medicine and Biology Society (EMBC), 35th Annual International Conference of the IEEE, Jul. 3, 2013, pp. 1522-1525.

Luo et al., Fibrosis of collagen i and. remodeling of connexin 43 in atrial myocardium of patients with atrial fibrillation. Cardiology. 2007; 107:248-253.

Mahnkopf al., Evaluation of the left atrial substrate inpatients with lone atrial fibrillation using delayed-enhanced MRI: Implications for disease progression and response to catheter ablation. Heart Rhythm. 2010; 7.1475-1481.

Maleckar et al., Electrotonic coupling between human atrial myocytes and fibroblasts alters myocyte excitability and repolarization. BiophysJ. 2009; 97:2179-2190.

McDowell et al., Mechanistic inquiry into the role of tissue remodling in fibrotic lesions in human atrial fibrillation. BiophysJ. 2013; 104:2764.

McDowell et al., Methodology for patient-specific modeling of atrial fibrosis as a substrate for atrial fibrillation. J Electrocardiol. 2012; 45:640-645.

McDowell et al., Susceptibility to arrhythmia in the infarcted heart depends on myofibroblast density. Biophys J. 2011; 101:1307-1315.

Miragoli et al., Electrotonic modulation of cardiac impulse conduction by myofibroblasts. Circ Res. 2006; 98:801-810.

Miyasaka et al., Secular trends in incidence of atrial fibrillation in Olmsted county, minnesota, 1980 to 2000, and implications on the projections for future prevalence. Circulation. 2006; 114:119-125.

Morita et al., Increased susceptibility of aged hearts to ventricular fibrillation during oxidative stress. Am J Physiol Heart Circ Physiol. 2009; 297:H1594-1605.

Nademanee et al., A new approach for catheter ablation of atrial fibrillation: Mapping of the electrophysiologic substrate. J Am Coll Cardiol. 2004; 43:2044-2053.

Narayan et al., Treatment of atrial fibrillation by the ablation of localized sources: Confirm (conventional ablation for atrial fibrillation with or without focal impulse and rotor modulation) trial. J Am Coll Cardiol. 2012; 60:628-636.

Pandit et al., "Rotors and the Dynamics of Cardiac Fibrillation", Circulation Research, Mar. 1, 2013, vol. 12, Issue 5, pp. 849-862.

Pedrotty et al., Cardiac fibroblast paracrine factors alter impulse conduction and ion channel expression of neonatal rat cardiomyocytes. Cardiovasc Res. 2009; 83:688-697.

Prassi et al., Automatically generated, anatomically accurate meshes for cardiac electrophysiology problems. IEEE Trans Biomed Eng. 2 pp. 9; 56:1318-1330.

Rook et al., Differences in gap junction channels between cardiac myocytes, fibroblasts, and heterologous pairs. American Journal of Physiology. 1992; 263:0959-0977.

Sanchez et al., Identification of transmural necrosis along a linear catheter ablation lesion during atrial fibrillation and sinus rhythm. J Intery Card Electrophysiol. 2003; 8:9-17.

Sanjiv et al., "Direct or Coincidental Elimination of Stable Rotors or Focal Sources May Explain Successful Atrial Fibrillation Ablation On-Treatment of the CONFIRM Trial (Conventional Ablation for AF With or Without Focal Impulse and Rotor Modulation", Journal of the American College of Cardiology, vol. 62, No. 2, Apr. 3, 2013, pp. 138-147.

Soon-Sung et al., "A patent-specific model of cirtual ablation for atrial fibrillation", Engineering in Medicine and Biology Society (EMBC), 2013 35th Annual International Conference of the IEEE, Jul. 3, 2013, pp. 1522-1525.

Tanaka et al., Spatial distribution of fibrosis governs fibrillation wave dynamics in the posterior left atrium during heart failure. Circ Res. 2007; 101:839-847.

Tanner et al., Trigger activity more than three years after left atrial linear ablation without pulmonary vein isolation inpatients with atrial fibrillation. Journal of the American College of Cardiology. 2005; 46.338-343.

Vadakkumpadan et al., Imagebasedestimation of ventricular fiber orientations for personalized modeling of cardiac electrophysiology. IEEE Trans Med Imaging. 2012; 31:1051-1060.

Vasquez et al., Enhanced fibroblast-myocyte interactions in response to cardiac injury. Circ Res. 2010; 107:1011-1020.

(56) References Cited

OTHER PUBLICATIONS

Vigmond et al., Computational tools for modeling electrical activity in cardiac tissue. J Electrocardiol. 2003; 36 Suppl: 69-74.
Xu et al., Atrial extracellular matrix remodeling and the maintenance of atrial fibrillation. Circulation. 2004; 109:363-368.
Zlochiver et al., Electrotonic myofibroblast-to-myocyte coupling increases propensity to reentrant arrhythmias in two-dimensional cardiac monolayers. Brophys J. 2008; 95:4469-4480.
International Search Report and Written Opinion issued in PCT Application No. PCT/US2014/068215 dated Mar. 17, 2015.

PERSONALIZED COMPUTATIONAL MODELING OF ATRIAL FIBROSIS TO GUIDE CATHETER ABLATION OF ATRIAL FIBRILLATION

RELATED APPLICATIONS

This application is a continuation of U.S. patent application Ser. No. 17/076,091, filed on Oct. 21, 2020, now allowed, which is a continuation of U.S. patent application Ser. No. 15/814,053, filed on Nov. 15, 2017, now U.S. Pat. No. 10,813,698, which is a continuation of U.S. patent application Ser. No. 14/094,334, filed on Dec. 2, 2013, now abandoned, all of which are hereby incorporated by reference in their entireties.

GOVERNMENT SUPPORT CLAUSE

This invention was made with government support under HL103428 and HL105216 awarded by the National Institutes of Health (NIH). The government has certain rights in the invention.

BACKGROUND

1. Field of Invention

The field of the currently claimed embodiments of this invention relates to systems and methods for identifying one or more ablation locations in a cardiac tissue region in an atrial fibrillation (AF) patient.

2. Discussion of Related Art

Atrial fibrillation (AF) is the most common arrhythmia in humans. AF affects over 2 million people in the United States alone, and data suggests that its prevalence will continue to increase as the population ages[1,2]. Ectopic beats originating from the pulmonary veins (PVs) in the left atrium (LA) have been identified as a trigger that initiates AF[3], Catheter-based ablation, the delivery of heat to destroy the ability of cardiac tissue to generate and conduct electrical signals locally, has emerged, over the last decade, as a promising treatment option; the procedure has successfully targeted the AF trigger via PV electrical isolation[4]. However, only a 70% success rate in achieving freedom from AF is reported with this approach[5].

In an attempt to increase the success rate of the therapy, recent ablation strategies have begun to target atrial tissue in the LA wall as the substrate that perpetuates AF. These strategies include substrate ablation guided by the spatial distribution of complex fractionated atrial electrograms[6] and/or dominant frequencies. A promising ablation strategy has recently emerged[8], which involves identifying and ablating AF localized rotors in the substrate The variable success rates of these strategies highlight the fact that identifying which components of the substrate sustain AF is critical for the correct identification of the targets for ablation.

Clinical evidence has demonstrated that the extent of atrial fibrosis is correlated with both AF incidence[9] and recurrence after ablation[10], highlighting its critical role in AF pathogenesis. Recent studies have also shown that the spatial distribution of fibrosis impacts AF dynamics[11,12], suggesting that the unique distribution of atrial fibrosis in each patient may govern the location of AF rotors, and could therefore potentially be used to identify critical targets for AF ablation, using a patient-specific approach.

Therefore, there remains a need for improved systems and methods for identifying one or more ablation locations in a tissue region in an atrial fibrillation (AF) patient.

SUMMARY

A method for identifying one or more ablation locations in an atrial tissue region in an atrial fibrillation (AF) patient with atrial fibrosis according to an embodiment of the current invention includes receiving three-dimensional imaging data representing the atria of the patient; generating a patient-specific model of AF from the three-dimensional imaging data; conducting simulation on the patient-specific atrial model to identify AF-perpetrating regions; and identifying from the AF-perpetrating regions one or more ablation locations in the atria.

A non-transitory computer-readable medium comprising computer-executable code for identifying one or more ablation locations in an atrial tissue region in an atrial fibrillation (AF) patient with atrial fibrosis according to an embodiment of the current invention includes computer-executable code comprising instructions that, when executed by the computer, causes the computer to: receive three-dimensional imaging data representing the atria of the patient; generate a patient-specific model of AF from the three-dimensional imaging data; conduct a simulation on the patient-specific atrial model to identify AF-perpetrating regions; and identify from the AF-perpetrating regions one or more ablation locations in the atria.

A system for identifying one or more ablation locations in an atrial tissue region in an atrial fibrillation (AF) patient with atrial fibrosis may include a processor configured to: receive three-dimensional imaging data representing the atria of the patient; generate a patient-specific model of AF from the three-dimensional imaging data; conduct a simulation on the patient-specific atrial model to identify AF-perpetrating regions; and identify from the AF-perpetrating regions one or more ablation locations in the atria. The system may be coupled to a memory that one or more instructions for configuring the processor or causing the processor to configured in any manner described herein.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Further objectives and advantages will become apparent from a consideration of description, drawings, and examples.

DETAILED DESCRIPTION

Figures 1A, 1B, 1C, 1D:
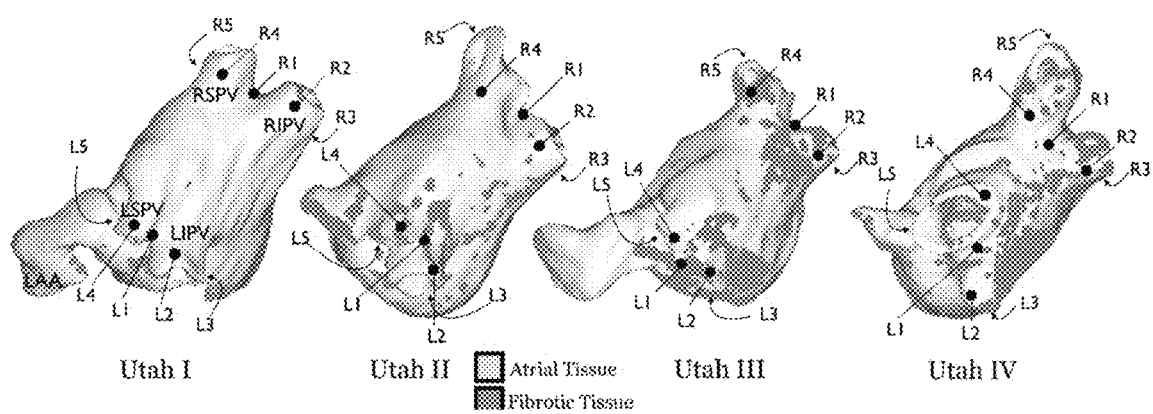
FIGS. 1A-1D depict patient-specific distributions of LA fibrosis for substrates Utah I-IV. Pacing locations in the left PVs (L1-LS) and right PVs (R1-RS) are indicated for each substrate. Anatomical locations for the left superior PV (LSPV), left inferior PV (LIPV), right superior PV (RSPV), right inferior PV (RIPV), and LA appendage (LAA) are indicated in the left-most substrate; all substrates are presented in identical orientations.

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification, including the Background and Detailed Description sections, are incorporated by reference herein in their entireties as if each had been individually incorporated.

The following abbreviations and acronyms may be used throughout this disclosure: AF: atrial fibrillation; PV: pulmonary vein; LA: left atrium; LGE-MRI: late gadolinium-enhanced magnetic resonance imaging; VREST: resting membrane potential; APD: action potential duration; $I_{K(ACh)}$: acetylcholine-activated potassium current; Cx: Connexin; LSPV: left superior pulmonary vein; LIPV: left inferior pulmonary vein; RSPV: right superior pulmonary vein; RIPV: right inferior pulmonary vein; and LAA: left atrial appendage.

According to some embodiments of the current invention, we determine how the spatial distribution of atrial fibrosis governs AF initiation and maintenance. Specifically, we aimed to demonstrate that virtual electrophysiological study that combines i) the anatomical structure and morphology of the patient atria and the unique distribution of atrial fibrosis as quantified from clinical MRI scans in vivo, and ii) computer modeling of electrophysiology of the atria could be used to predict: (1) how the unique patient-specific atrial fibrosis distribution determines the locations from which ectopic stimuli will degrade into reentrant activity in the fibrotic substrate; (2) the dynamic behavior of persistent AF rotors in the individual atrial substrate; and (3) the optimal locations of ablation of the fibrotic substrate in each patient. To achieve the study goal, we constructed four patient-specific atrial models with distributed fibrosis generated from high-resolution late gadolinium-enhanced magnetic resonance images (LGE-MRI) acquired in vivo from patients suffering from atrial arrhythmias. Fibrotic lesions were modeled with electrophysiological properties that were distinct from non-fibrotic regions; simulations were conducted with dynamic pacing from different, predominantly PV, locations and analysis was performed to determine how fibrotic lesions led to the breakup of pacing-induced wavefronts and their degeneration into reentrant waves, and to the spatial localization of the resulting AF rotors. Finally, simulations were performed to demonstrate that AF could be rendered non-inducible by ablating the fibrotic substrate at locations determined on the basis of knowledge regarding the spatial localization of AF rotors. The simulations may be conducted on the personalized model in order to determine the regions of tissue which maintain the persistent electrical rotors, and ablation lesions may be simulated within these regions to determine the size and shape of the ablation lesion necessary to render the substrate non-inducible to AF. The simulations and analysis may be performed after the LGE-MRI images are captured for the screening process but before an individual undergoes ablation.

The identification of ablation lesions via personalized simulations has the potential to improve outcomes of catheter ablation, shorten the duration of each procedure, and limit the number of repeat procedures.

Methods

A group of patients with atrial arrhythmias presenting to the University of Utah for catheter ablation underwent late LGE-MRI acquisition at a resolution of 1250×1250×1500 µm³, following the methodology of Akoum et al[13]. The extent of pre-ablation LA fibrosis was quantified[13], and each patient was stratified into one of four groups: Utah I (<5% LA wall enhancement), Utah II (>5% to <20), Utah III (>20% to <35), or Utah IV (>35). One set of patient data from each of these groups was selected for use in this computational study; the simulations were blinded to the patient history. The amount of LA fibrosis was quantified as 0.8%, 18.0%, 22.8%, and 42.0% for the selected 4 patients from categories Utah I-IV, respectively.

Patient-Specific Modeling

We have recently developed a pipeline for the generation of a 3D patient-specific geometry of the' atria with accurate distribution of fibrosis[14]. This pipeline was used here for the creation of the four biophysically detailed fibrotic patient-specific LA models, each from a different Utah category. In this study, we modeled only the LA due to the fact that the clinical correlations drawn. between fibrosis and AF recurrence following ablation were based on quantification of fibrosis in the LA only[10].

FIGS. 1A-1D depict patient-specific distributions of LA fibrosis for substrates Utah I-IV. Briefly, LGE-MRI image segmentation and interpolation was used to produce a high-resolution image of the LA wall with accurate fibrotic lesion distribution for each of the four patients (FIG. 1). A finite element tetrahedral mesh was generated from each of the segmented image stacks of the LA,[15] and fiber orientation was estimated as previously described[14,16]. Non-fibrotic regions of the tissue were represented with a modified version of the Courtemanche-Ramirez-Nattel model of the human atrial action potential under AF conditions[17], as described by Krummen et al[18]; the model also included the formulation of the acetylcholine-activated potassium current, $I_{K(ACh)}$, from Kneller et al.[19] Conductivities were chosen such that conduction velocity fell within the range recorded in the human atrium[20], as described in ref[12]. Although this is one way to represent the electrophysiology of the atria, there are many other ways of representing the electrophysiology of the atria, and any of them may also be used with the systems, media, and methods discussed herein.

In our previous study[12] we examined several different representations of fibrotic remodeling in a patient-specific model with extensive fibrosis, generated from a patient suffering persistent AF, to investigate how each mechanistically contributed to AF propensity. In that study we determined that sustained AF resulting from PV pacing matched the AF clinical manifestation when the patient's extensive fibrotic lesions were modeled with a three-component representation of fibrosis, based on experimental evidence. The three aspects of remodeling were: (1) diffuse collagen deposition, (2) gap junction remodeling due to connexin 43 (Cx43) protein down-regulation and lateralization, and (3) fibroblast proliferation and phenotype switching into myofibroblasts. Based on our previous findings, we incorporated these three aspects of remodeling into the fibrotic lesions of each of the four patient-specific models in order to determine how the distribution of fibrosis governs the potential degeneration of pacing-induced wavefronts into reentrant circuits as well as the dynamic behavior of the resulting AF rotors.

Diffuse collagen deposition was represented by employing a method of 3D element decoupling to introduce fine conduction barriers along fiber orientation in the fibrotic lesions, as previously described[12,14]. Gap junction down-regulation and lateralization was accounted for, as previously described[12], by altering conductivities to represent the 31 30% reduction in Cx43 expression in atria in AF compared to sinus rhythm[21], as well as the 3.9-fold higher lateral Cx43 labeling in atrial myocytes in AF compared to sinus rhythm[22]. Lastly, myofibroblasts were randomly assigned to 1% of the fibrotic lesions and formed electrical connections with adjacent myocytes, as observed experimentally[23,24]; myofibroblast membrane kinetics were modeled following our previously published methodology[4,25]. Our previous study demonstrated that myofibroblast influences can be equivalently modeled via electrical coupling or paracrine effects[12]. Although this is one way to represent fibrosis, there are many other ways of representing the fibrosis, and any of them may also be used with the systems, media, and methods discussed herein.

Simulation Protocol and Data Analysis

Mathematical description of current flow was based on the monodomain representation of the myocardium and simulations were executed using the simulation package CARP (CardioSolv LLC)[26]. To investigate how the distribution of fibrosis determines whether dynamic pacing will degrade into reentrant activity and initiate AF, ten pacing locations were chosen in each substrate to represent ectopic triggers. Stimulus locations were distributed around the PVs (where most ectopic beats originate[3]) such that five stimuli were located within the left PVs (stimuli L1-L5 in each LA model, FIG. 1) and five were located within the right PVs (stimuli R1-R5 in each LA model, FIG. 1). Specifically, two pacing sites were located on opposing sides of each PV, one site was located between the left PVs, and one site was located between the right PVs. For each pacing location, a dynamic pacing protocol was used to assess arrhythmia inducibility, as performed clinically[8]. The protocol consisted of pacing for 5 beats at a 365 ms cycle length, followed by two beats at cycle lengths of each of the following: 290 ms, 285 ms, 280 ms, 275 ms, 270ms, 268 ms, 266 ms, 264 ms, 262 ms, and 260 ms. Sustained AF was defined as fibrillatory activity lasting for 10 seconds after the delivery of the last stimulus. Additional stimuli were placed as necessitated by initial simulation results.

In order to investigate how patient-specific distributions of atrial fibrosis govern AF initiation and maintenance, the following analysis was performed:
- To determine if simulations using the patient-specific models could accurately represent the ability of an LA substrate to support AF, the simulations were performed blinded to patient history. Substrates in which stimuli from one or more locations initiated AF were considered susceptible to AF. Predictions were considered accurate if the simulation outcomes (susceptible vs. not susceptible to AF) accurately matched the patient's clinical history.
- To assess the influence of fibrotic lesion distribution on AF inducibility from different PV pacing locations, the distance between each stimulus site and its closest fibrotic lesion was calculated in substrates in which AF was observed.

Identifying Rotors and Representing Ablation

In models in which AF resulted from PV pacing, phase singularities (rotor organizing centers) were calculated over a period of 10 seconds, and the phase singularity meander quantified for each rotor. Ablation lesions were implemented in the models to target the regions of tissue which maintained the persistent phase singularities. Lesions were modeled as one or more transmural regions[31] of inexcitable tissue; they were circular to account for catheter tip shape, and 7 mm in diameter (within the range of clinical ablation lesions[8]). Arrhythmia inducibility was tested after the implementation of each ablation lesion until AF could no longer be initiated following dynamic pacing.

Results

Arrhythmia Inducibility in Patient-Specific Models

Substrate propensity to AF was initially tested from the ten PV locations in each of the four patient-specific models of the fibrotic LA. Neither the Utah I nor the Utah II substrates gave rise to arrhythmia following pacing from any of the ten locations. The Utah III substrate gave rise to sustained AF following pacing from two of the ten pacing locations; those were pacing sites L2 and L4 (as marked in FIG. 1). Pacing from three of the ten PV locations (L1, L4, and R1, as seen in FIG. 1) resulted in sustained AF in the Utah IV substrate.

Figure 2:
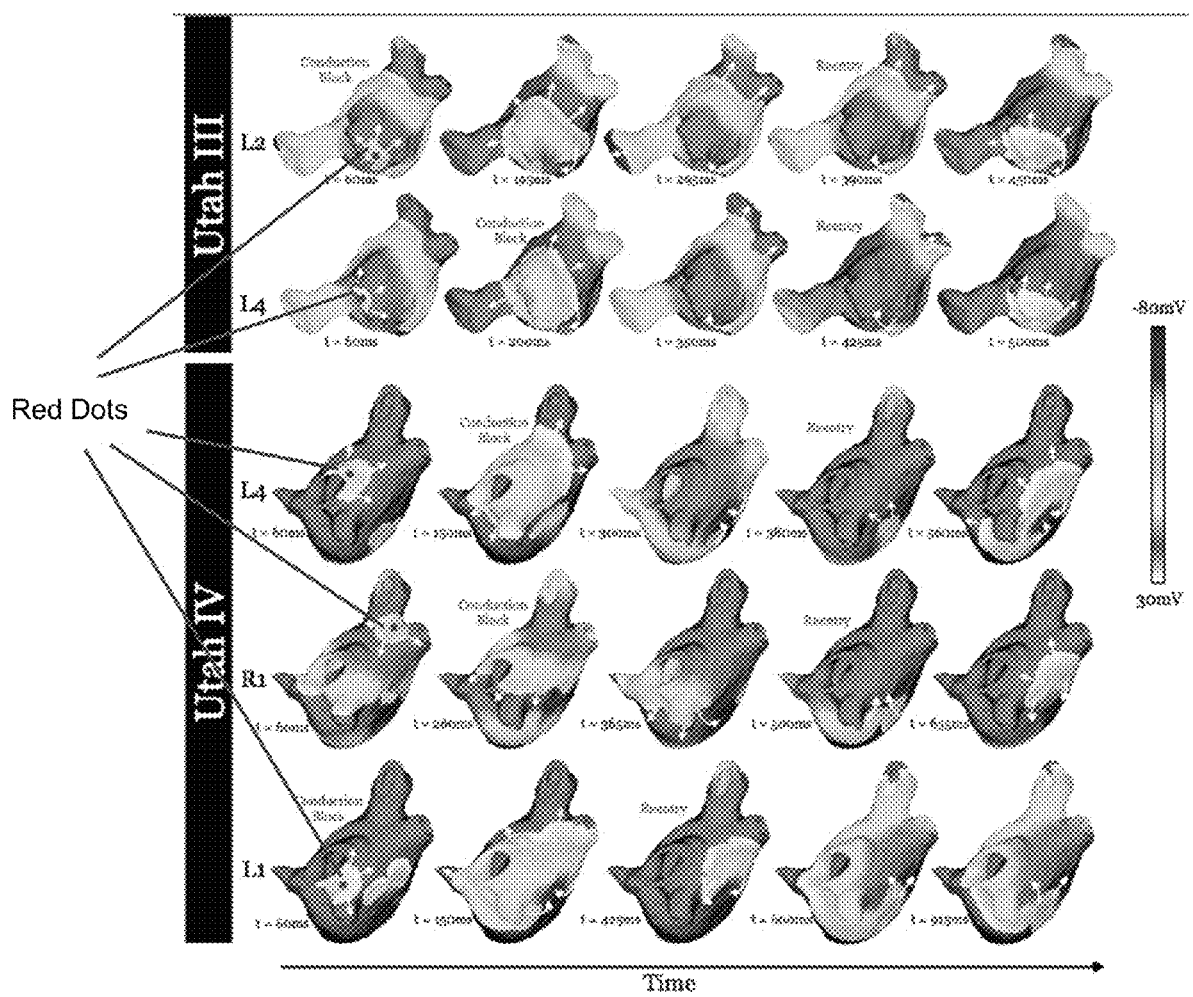
FIG. 2 depicts transmembrane potential maps at five time instants, documenting AF initiation in substrates Utah III (top two rows) and Utah IV (bottom three rows) from different PV pacing locations (as noted at left). Lines of block are marked in red. White arrows indicate direction of propagation. Darker areas (left-most column) indicate pacing location.

FIG. 2 presents the events leading to the formation of the first cycle of reentry resulting from dynamic pacing at locations that initiated AF in substrates Utah III and Utah IV. In each case, unidirectional conduction block (as denoted by the red lines in FIG. 2) took place. It resulted from either the stimulus-induced wavefront encountering tissue in a refractory state (Utah IV: R1) or the collision of the stimulus-induced wavefront with the wavefront that was the result of the preceding beat from the pacing protocol (Utah III: L2 and L4; Utah IV: L1 and L4). The latter case was possible because of the slow and discontinuous conduction that occurred in the large fibrotic lesions in substrates Utah III and Utah IV, resulting in the wave taking a propagation direction different from that in nonfibrotic tissue. Following unidirectional conduction block in substrates Utah III and Utah IV, a reentrant circuit was formed, marking AF onset.

After the computational study was complete, patient history was provided to our team. In all substrates, simulation outcomes faithfully represented the patient clinical manifestation. The patients from which the Utah I and II LA models were generated did not suffer from AF, while the patients whose scans were used to create the Utah III and IV LA models both suffered from AF.

Distribution of Atrial Fibrosis Determines Whether Paced Beats Degrade into AF

The results from our simulations revealed that all stimuli of the dynamic pacing protocol were delivered in all cases in which AF was initiated (i.e., in these cases the dynamic pacing protocol, which consisted of pacing starting at cycle lengths of 365 ms and proceeding down to 260 ms, resulted in reentry formation). In most cases in which AF was not initiated by pacing from a given PV site in substrates Utah III and IV, a stimulus from the pacing train failed to excite tissue and pacing-induced propagation thus failed before the pacing protocol was completed (that is, prior to reaching cycle lengths of 260 ms). The observation that AF ensued only after propagation was elicited following the shortest pacing cycle lengths in the dynamic pacing protocol is consistent with experimental findings that show short effective refractory periods are significantly correlated with an increased probability of sustained AF[27].

We have previously demonstrated that the electrophysiological effects of fibrosis in the atria extends beyond the borders of fibrotic lesions themselves, well into non-fibrotic tissue[12]. Indeed, APD changes occur in non-fibrotic tissue due to influences from nearby fibrosis; the extent of APD changes attenuates with the distance from the fibrotic lesion[25]. Therefore, given that repolarization dynamics throughout the LA are altered non-uniformly by fibrosis, in a distance-to-fibrotic-region-dependent manner, we sought to determine how a PV pacing location's distance to the region of fibrosis affects the ability of a stimulus from that location to elicit excitation in the LA in the Utah III and IV models. To perform this analysis, the distance between each PV pacing site and its closest fibrotic lesion was plotted against the pacing cycle length of the stimulus from that location's pacing train that failed to elicit excitation in substrates Utah III and IV.

Figure 3:
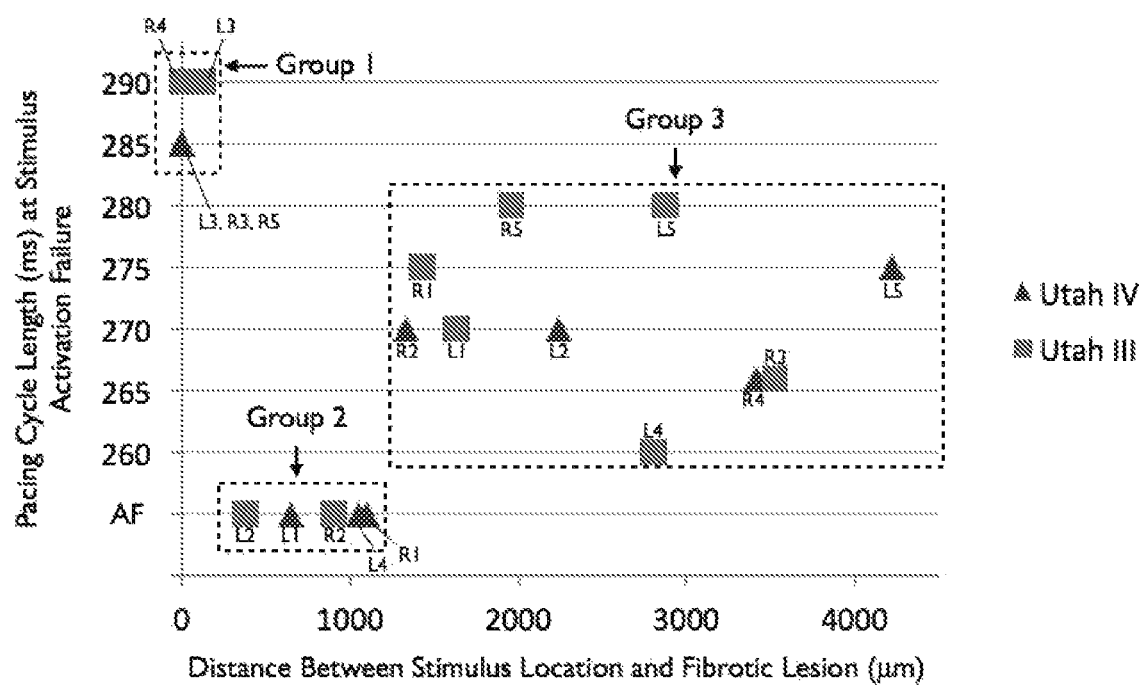
FIG. 3 depicts a plot of the distance between each pacing site and its closest fibrotic lesion vs. the pacing cycle length at which a stimulus either failed to excite the tissue or resulted in AF in substrates Utah III (red squares) and Utah IV (blue triangles). Stimulus locations are labeled for each data point. Groups 1-3 are indicated for discussion purposes.

Results are presented in FIG. 3. In cases when AF was initiated, the cycle length is 260 ms, the shortest cycle length in the pacing protocol. The graph demonstrates a clustering of three groups of data points: Group 1, PV pacing locations for which there was a fibrotic lesion in close proximity (<120 μm) and for which stimuli with cycle lengths of 285-290 ms in the pacing protocol failed to excite the tissue; Group 2, PV pacing locations that were between 378 and 1052 μm from fibrotic lesions and for which sustained AF resulted following the execution of the entire dynamic pacing protocol; and Group 3, stimulus locations that were far from fibrotic lesions (>1330 μm) and for which stimuli with cycle lengths of 260-280 ms failed to excite the tissue.

Based on the finding that stimuli that are located at a distance between 378 and 1052 μm from fibrotic lesions can initiate AF in models Utah III and IV, the distance between each point in the non-fibrotic tissue and the closest fibrotic lesion was calculated to determine what locations would fall within the range of "sweet spot" distances to fibrotic lesions and could therefore be considered "prime ectopic spots" for AF initiation. We found that "prime" locations comprise 3.56% and 4.43% of LA volume (including the PVs) in the Utah III and IV models, respectively. A disproportionately large amount of this "prime" tissue was localized in the PVs, 19.78% and 32.56% in the Utah III and IV substrates, respectively, although the PVs comprised only 14.9% and 22.93% of total tissue volume, respectively, in these models. Building on this finding, pacing trains were delivered from two locations in "prime" tissue outside of the PV regions in substrates Utah III and IV to test AF inducibility; consistent with our predictions above, sustained AF was initiated by pacing from these locations following the dynamic protocol (data not shown).

Distribution of Atrial Fibrosis Determines AF Rotor Location

Figure 4:
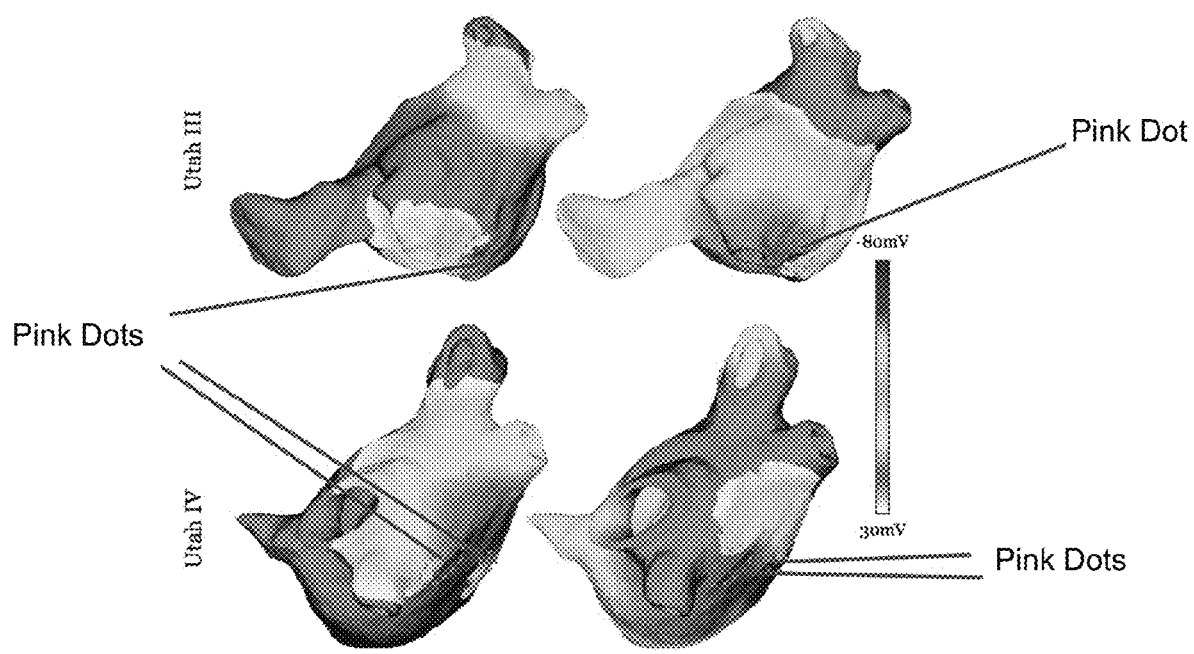
FIG. 4 depicts transmembrane potential maps at two time instants in substrates Utah III (top row) and Utah IV (bottom row) demonstrating the meandering of the mother rotor organizing centers termed phase singularities (shaded areas). Regions of meander are outlined with dashed lines.

Epicardial phase singularities were calculated in all of the cases in which pacing resulted in AF initiation. Phase singularities, as opposed to filaments, were examined due to the fact that the walls of the LA are thin (<3 mm) as well as for ease of analyzing the meandering of the rotor organizing centers over time in our models. In the Utah III and IV models AF was characterized with the formation of one or more mother rotors, which persisted for the duration of the AF simulations, as well as other "breakoff" fibrillatory activity, the phase singularities of which appeared and vanished quickly. Once AF was initiated, the phase singularities associated with the persistent reentries meandered within the same tissue regions in each substrate, regardless of the pacing location from which AF was induced, indicating that the patient-specific distribution of fibrosis, rather than the location of atrial trigger, was the most important factor governing AF mother rotor location(s). In the Utah III substrate, one persistent (mother rotor) phase singularity was found to meander within an approximately oval region of tissue with long and short diameters of 13.2 mm and 6.7 mm, respectively (FIG. 4, top row; mother rotor phase singularities locations at the given instant of time are shown by the pink dots; regions of meander are outlined by red dashed line). In the Utah IV substrate, there were two persistent phase singularities, one meandering within a larger oval region of tissue with long and short diameters of 13.7 mm and 6.2 mm, respectively, and one meandering in a smaller approximately circular region of tissue that was 6.6 mm in diameter (FIG. 4, bottom row).

Figure 5:
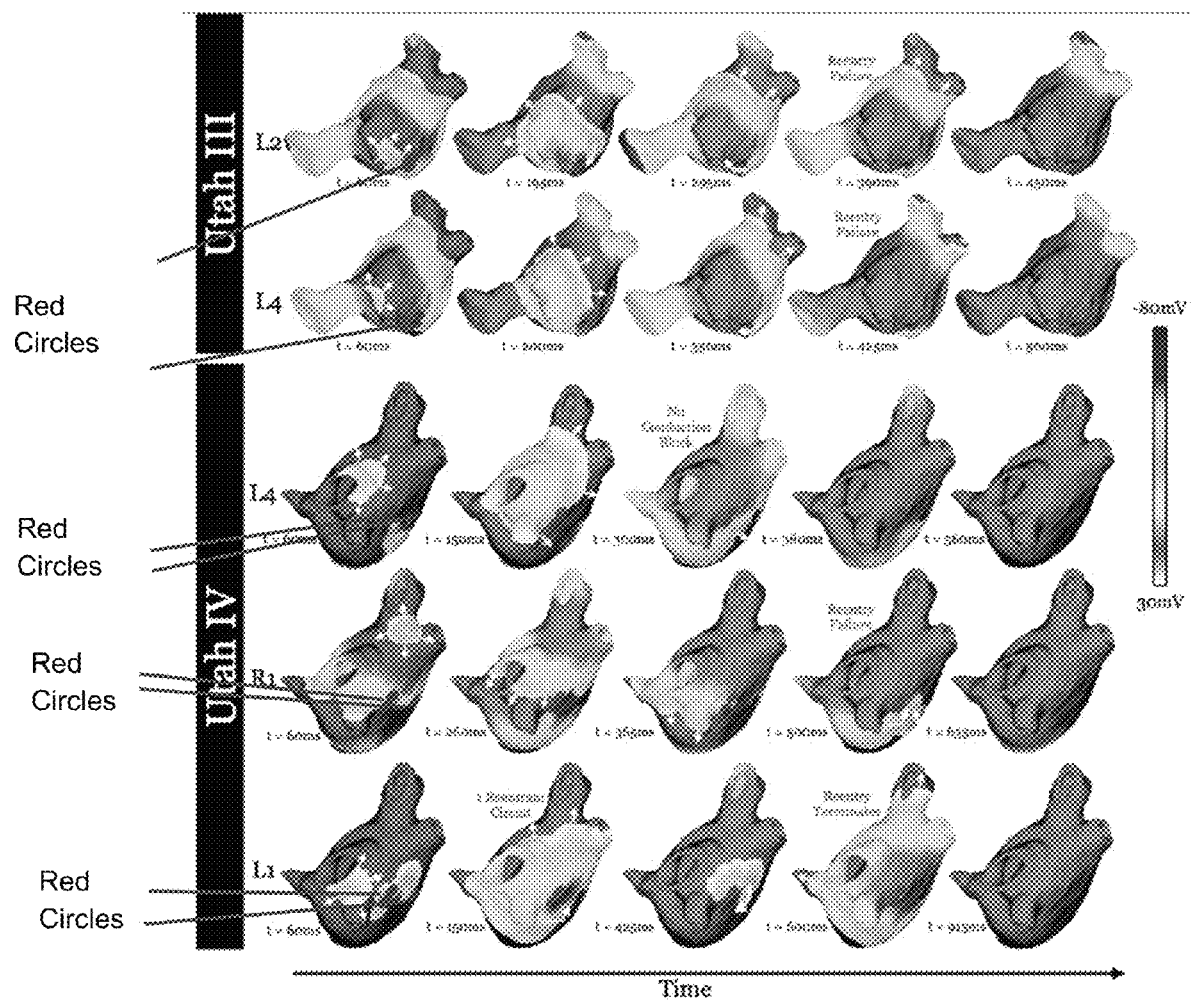
FIG. 5 depicts transmembrane potential maps at five time instants in substrates Utah III (top two rows) and Utah IV (bottom three rows) from different pacing locations (as noted at left) with ablation lesions modeled. Red circles (as indicated in the figure and in left-most column) indicate the extent of ablation lesions. White arrows indicate direction of propagation. Time instances and pacing locations are identical to those presented in FIG. 2.

Ablation was applied, as described in Methods, to regions within which the persistent (mother rotor) phase singularities (which are the rotor organizing centers) meandered. Snapshots of transmembrane potential distributions at time instants throughout simulations with ablation lesions modeled are shown in FIG. 5; the selected time instants are identical to those presented in FIG. 2 to allow for comparison. The implementation of ablation consisting of two overlapping circular lesions (indicated in red in the left-most images in FIG. 5), fully covering the long diameter (13.2 mm) of the region of mother rotor phase singularity meander was necessary to result in AF non-inducibility in the Utah III substrate following pacing train delivery from both the L2 and L4 locations. In the Utah IV substrate, two separate ablations were implemented to render inexcitable the regions of meander of the two persistent phase singularities. The smaller region of meander was targeted with one circular ablation, while the larger region of meander was targeted with two overlapping circular lesions to again fully cover the long diameter of the region of persistent phase singularity meander (13.7 mm). The ablations (indicated in red in the left-most substrates in FIG. resulted in AF non-inducibility following pacing from all three original locations (L1, L4, and R4) in the Utah IV substrate. It was not possible to achieve AF non-inducibility with fewer or smaller ablation lesions.

Discussion

This study demonstrates the feasibility of using a patient-specific simulation approach to predict the role of the unique atrial fibrotic distribution in the dynamics of the patient's persistent AF. The study elucidated how patient-specific fibrosis distribution determines whether ectopic stimuli result in persistent AF, and from which specific atrial locations. We evaluated the dynamic behavior of persistent AF rotors in the patient atria; based on this analysis, and particularly, on the predicted spatial localization of persistent AF rotors, we performed feasibility simulations showing that AF could be rendered non-inducible, in a patient-specific approach, by ablating regions of persistent rotor meander in the fibrotic substrate. The present study has, thus, two contributions, each discussed below: one in mechanistic understanding of the role of the fibrotic substrate in persistent AF, and another, in demonstrating that it is feasible to identify the optimal targets of atrial ablation in the patient using the approach presented here prior to the clinical procedure. The main mechanistic findings in this study are:

(1) The mechanisms which determine whether pacing from a given atrial site will degrade into AF, operate in a distance-to-fibrosis-dependent fashion, with pacing from locations only in the mid-range of distances (378-1052 µm) to fibrotic lesions resulting in sustained AF.

(2) A disproportionate amount of all non-fibrotic tissue that falls in the mid-range (i.e arrhythmogenic "sweet spot") distance to fibrotic lesions is located in the PVs.

(3) Patient-specific distribution of fibrosis, rather than location of pacing (i.e. location of arrhythmia trigger), governs AF "mother rotor" location(s) and meander; phase singularities associated with persistent reentries meander within the same tissue regions once AF is initiated, regardless of the pacing location.

In this study, two out of ten PV stimulus locations resulted in AF initiation in the Utah III substrate (with 22.8% fibrosis), while three out of ten PV stimulus locations caused AF in the Utah IV substrate (with 42.0% fibrosis); no PV stimuli caused AF in the Utah I and II models. This finding demonstrates a correlation between the amount of fibrosis and the probability of a trigger initiating AF; it is consistent with the correlation found between AF incidence and percent fibrosis in the LA[9], the underlying cause of which has remained unknown. Our study findings suggest a new paradigm, that AF incidence may be higher in patients with more fibrosis due to the fact that larger degrees of fibrosis cause locations in the substrate to become "prime" for triggering AF. Indeed, we demonstrated that "prime" trigger locations comprise 3.56% and 4.43% of the Utah III and IV substrates by volume, respectively, of which disproportionate amounts were located in the PVs. The concept that ablation may eliminate "prime" tissue may help explain the perplexing clinical finding that triggered activity, which can remain frequent years after linear LA ablation, often does not initiate AF[37]. Should linear LA ablation eliminate "prime" tissue itself or create an electrical barrier that prevents fibrotic lesions from altering nearby tissue electrophysiology, such that "prime" regions are not created, substrates could be rendered noninducible to AF, despite the presence of triggered activity.

Traditionally, AF treatments have either been aimed at suppressing atrial triggers that initiate AF[4], or at modifying the substrate that sustains it[6,7]. In this study, however, the spatial distribution of atrial fibrosis was found both to determine whether pacing initiates AF and to govern the dynamics of the resulting AF rotors. The fact that the distribution of atrial fibrosis modulates both AF initiation and its maintenance creates a new paradigm for AF treatment, in which one treatment strategy could possibly target both AF-triggering and -perpetuating mechanisms. Indeed, this study demonstrated that in all cases when the regions of meander of persistent phase singularities were ablated, reentrant circuits could not form following pacing from locations that had previously resulted in sustained AF (FIG. 5). This concept may explain why a novel ablation strategy, aimed at ablating AF electrical rotors, has reported a higher degree of successful patient outcomes as compared to PV electrical isolation[8]. Consistent with our finding that the implementation of 1 to 2 ablation lesions led to AF non-inducibility, Narayan et al. reported that an average of 2.1+1.0 electrical rotors were observed in patients with sustained AF, and that the ablation of these rotors led to successful termination of AF[8].

This study was conducted without knowledge of the history of the patients the scans of whom were used to create the models; the simulations accurately predicted the clinical outcome of each of the four patients. Indeed, models which resulted in AF (Utah III and IV) turned out to have been generated from patients suffering AF, while models which did not result in AF (Utah I and II), turned out to have been derived from AF-free patients. Our proof-of-concept simulations thus indicate that patient-specific modeling of atrial arrhythmogenesis under fibrotic conditions could become in the future a powerful new non-invasive tool to stratify atrial arrhythmia risk.

In this study we demonstrated that a virtual electrophysiological study using patient-specific atrial models could provide a novel way to identify regions of meander of persistent (mother rotor) phase singularities based on the individual spatial distribution of fibrosis. We showed that ablating these regions of meander in the models results in AF non-inducibility from any stimulus location. This study therefore presents the proof-of-concept of a non-invasive approach to the identification of the ablation targets for persistent AF in the fibrotic atria. In its translation to the clinic, we envision that the approach will entail the use, prior to the clinical procedure, of an MRI-based subject-specific multiscale electrophysiological model of the fibrotic atria to analyze AF dynamics and rotor meander, and to determine the targets of ablation. Once the targets of ablation are determined and visualized by the present approach, we envision that ablation delivery for AF termination could be swift and precise, eradicating, with a minimal number of lesions, all rotors in the fibrotic substrate. This could dramatically improve the efficacy of ablation, increase the tolerance for the procedure, and reduce post-procedure complications and long-term deleterious effects resulting from the lengthy invasive mapping and the numerous unnecessary ablation lesions.

Study Limitations

Because fibrosis was identified in the LA only, for computational tractability, simulations used only the LA to determine AF rotor dynamics and perform ablation. The methodology would not change when modeling both atria; similarly, the insights obtained here will remain the same. With additional fibrosis in the RA, persistent rotors might meander in the RA, necessitating ablation lesions there as well. Another limitation of the study is the small number of patient scans due to the low resolution of the scans. However, image resolution is likely to improve with time and advances in MRI technology, which will improve the utility of our approach.

FUNDING SOURCES

The authors gratefully acknowledge support of this work by the American Heart Association Predoctoral Fellowship to K. M and the National Institutes of Health (grants HL103428 and HL105216) to N. T. This work was also supported in part by the U.S. National Science Foundation, grant NSF-OCI-108849. We also acknowledge support for image processing and model generation software from the Center for Integrative Biomedical Computing (CIBC) at the University of Utah, sponsored by NIH Grant P41 GM103545-14.

REFERENCES

1. Feinberg W M, Blackshear J L, Laupacis A, Kronmal R, Hart R G. Prevalence, age distribution, and gender of patients with atrial fibrillation. Analysis and implications. Arch Intern Med. 1995; 155:469-473
2. Miyasaka Y, Barnes M E, Gersh B J, Cha S S, Bailey K R, Abhayaratna W P, Seward J B, Tsang T S. Secular trends in incidence of atrial fibrillation in Olmsted county, minnesota, 1980 to 2000, and implications on the projections for future prevalence. Circulation. 2006; 114:119-125
3. Haissaguerre M, Jais P, Shah D C, Takahashi A, Hocini M, Quiniou G, Garrigue S, Le Mouroux A, Le Metayer P, Clementy J. Spontaneous initiation of atrialfibrillation by ectopic beats originating in the pulmonary veins. N Engl J Med. 1998; 339:659-666
4. Haissaguerre M, Jais P, Shah D C, Garrigue S, Takahashi A, Lavergne T, Hocini M, Peng J T, Roudaut R, Clementy J. Electrophysiological end point for catheter ablation of atrial fibrillation initiated from multiple pulmonary venous foci. Circulation. 2000; 101.1409-1417
5. Cappato R, Calkins H, Chen S A, Davies W, lesaka Y, Kalman J, Kim Y H, Klein G, Natale A, Packer D, Skanes A, Ambrogi F, Biganzoli E. Updated worldwide survey on the methods, efficacy, and safety of catheter ablation for human atrial fibrillation. CircArrhythm Electrophysiol. 2010v332-38
6. Nademanee K, McKenzie J, Kosar E, Schwab M, Sunsaneewitayakul B, Vasavakul T, Khunnawat C, Ngarmukos T. A new approach for catheter ablation of atrial fibrillation: Mapping of the electrophysiologic substrate. J Am Coll Cardiol. 2004; 43:2044-2053
7. Atienza F, Almendral J, Jalife J, Zlochiver S, Ploutz-Snyder R, Torrecilla E G, Arenal A, Kalifa J, Fernandez-Aviles F, Berenfeld O. Real-time dominant frequency mapping and ablation of dominant frequency sites in atrial fibrillation with left-to-right frequency gradients predicts long-term maintenance of sinus rhythm. Heart Rhythm. 2009; 6:33-40
8. Narayan S M, Krummen D E, Shivkumar K, Clopton P, Rappel W J, Miller J M. Treatment of atrial fibrillation by the ablation of localized sources: Confirm (conventional ablation for atrial fibrillation with or without focal impulse and rotor modulation) trial. J Am Coll Cardiol. 2012; 60:628-636
9. Xu J, Cui G, Esmailian F, Plunkett M, Marelli D, Ardehali A, Odim J, Laks H, Sen L. Atrial extracellular matrix remodeling and the maintenance of atrial fibrillation. Circulation. 2004; 109:363-368
10. Mahnkopf C, Badger T J, Burgon N S, Daccarett M, Haslam T S, Badger C T, McGann C J, Akoum N, Kholmovski E, Macleod R S, Marrouche N F. Evaluation of the left atrial substrate inpatients with lone atrial fibrillation using delayed-enhanced MRI: Implications for disease progression and response to catheter ablation. Heart Rhythm. 2010; 7.1475-1481
11. Tanaka K, Zlochiver S, Vikstrom K L, Yamazaki M, Moreno J, Klos M, Zaitsev A V, Vaidyanathan R, Auerbach D S, Landas S, Guiraudon G, Jalife J, Berenfeld O, Kalifa J. Spatial distribution of fibrosis governs fibrillation wave dynamics in the posterior left atrium during heart failure. Circ Res. 2007; 101:839-847
12. McDowell K S, Vadakkumpadan F, Blake R, Blauer J, Plank G, MacLeod R, Trayanova N. Mechanistic inquiry into the role of tissue remodling in fibrotic lesions in human atrial fibrillation. BiophysJ. 2013; 104:2764
13. Akoum N, Daccarett M, McGann C, Segerson N, Vergara G, Kuppahally S, Badger T, Burgon N, Haslam T, Kholmovski E, Macleod R, Marrouche N. Atrial fibrosis helps select the appropriate patient and strategy in catheter ablation of atrial fibrillation: A DE -MRI guided approach. J Cardiovasc Electrophysiol. 2011; 22; 16-22
14. McDowell K S, Vadakkumpadan F, Blake R, Blauer J, Plank G, Macleod R S., Trayanova N A. Methodology for patient-specific modeling of atrial fibrosis as a substrate for atrial fibrillation. J Electrocardiol. 2012; 45:640-645
15. Prassl A J, Kickinger F, Ahammer H, Grau V, Schneider J E, Hofer E, Vigmond E J, Trayanova N A, Plank G. Automatically generated, anatomically accurate meshes for cardiac electrophysiology problems. IEEE Trans Biomed Eng. 2pp9; 56:1318-1330
16. Vadakkumpadan F, Arevalo H, Ceritoglu C, Miller M, Trayanova N. Imagebasedestimation of ventricular fiber orientations for personalized modeling of cardiac electrophysiology. IEEE Trans Med Imaging. 2012; 31:1051-1060
17. Courtemanche M, Ramirez R J, Nattel S. Ionic targets for drug therapy and atrial fibrillation-induced electrical remodeling: Insights from a mathematical model. Cardiovasc Res. 1999; 42:477-489
18. Krummen D E, Bayer J D, Ho J, Ho G, Smetak M R, Clopton P, Trayanova N A, Narayan S M. Mechanisms of human atrial fibrillation initiation: Clinical and computational studies of repolarization restitution and activation latency. CircArrhythm Electrophysiol. 2012; 5.1149-1159
19. Kneller J, Zou R Q, Vigmond E J, Wang Z G, Leon L J, Nattel S. Cholinergic atrial fibrillation in a computer model of a two-dimensional sheet of canine atrial cells with realistic ionic properties. Circulation Research. 2002; 90:E73-E87
20. Hanson A, Holm M, Blomstrom P, Johanson R, Luhrs C, Brandt J, Olsson S B. Right atrial free wall conduction velocity and degree of anisotropy in patients with stable sinus rhythm studied during open heart surgery. Eur HeartJ. 1998; 19:293-300
21. Luo M H, Li Y S, Yang K P. Fibrosis of collagen i and. remodeling of connexin 43 in atrial myocardium of patients with atrial fibrillation. Cardiology. 2007; 107: 248-253
22. Kostin S, Klein G, Szalay Z, Hein S, Bauer E P, Schaper J. Structural correlate of atrial fibrillation in human patients. Cardiovasc Res. 2Q02; 54:361-379
23. Du J, Xie J, Zhang Z, Tsujikawa H, Fusco D, Silverman D, Liang B, Yue L. Trpm7-mediated cat+ signals confer fibrogenesis in human atrial fibrillation. Circ Res. 2010; 106:992-1Q03.
24. Camelliti P, Green C R, LeGrice I, Kohl P. Fibroblast network in rabbit sinoatrial node: Structural and functional identification of homogeneous and heterogeneous cell coupling. Circ Res. 2004; 94:828-835
25. McDowell K S, Arevalo H J, Maleckar M M, Trayanova N A. Susceptibility to arrhythmia in the infarcted heart depends on myofibroblast density. Biophys J. 2011; 101:1307-1315
26. Vigmond E J, Hughes M, Plank G, Leon L J. Computational tools for modeling electrical activity in cardiac tissue. J Electrocardiol. 2003; 36 Suppl: 69-74
27. Byrd G D, Prasad S M, Ripplinger C M, Cassilly T R, Schuessler R B, Boineau J P, Damiano R J, Jr. Importance of geometry and refractory period in sustaining atrial fibrillation: Testing the critical mass hypothesis. Circulation. 2005; 112:17-13
28. Miragoli M, Gaudesius G, Rohr S. Electrotonic modulation of cardiac impulse conduction by myofibroblasts. Circ Res. 2006; 98:801-810
29. Vasquez C, Mohandas P, Louie K L, Benamer N, Bapat A C, Morley G E. Enhanced fibroblast-myocyte interactions in response to cardiac injury. Circ Res. 2010; 107:1011-1020
30. Kuo C S, Munakata K, Reddy C P, Surawicz B. Characteristics and possible mechanism of ventricular arrhythmia dependent on the dispersion of action potential durations. Circulation. 1983; 67:1356-1367
31. Sanchez J E, Kay G N, Benser M E, Hall J A, Walcott G P, Smith W M, Ideker R E. Identification of transmural necrosis along a linear catheter ablation lesion during atrial fibrillation and sinus rhythm. J Intery Card Electrophysiol. 2003; 8:9-17
32. Rook M B, Vanginneken A C G, Dejonge B, Elaoumari A, Gros D, Jongsma H J. Differences in gap junction channels between cardiac myocytes, fibroblasts, and heterologous pairs. American Journal of Physiology. 1992; 263:0959-0977
33. Pedrotty D M, Klinger R Y, Kirkton R D, Bursac N. Cardiac fibroblast paracrine factors alter impulse conduction and ion channel expression of neonatal rat cardiomyocytes. Cardiovasc Res. 2009; 83:688-697
34. Maleckar M M, Greenstein J L, Giles W R, Trayanova N A. Electrotonic coupling between human atrial myocytes and fibroblasts alters myocyte excitability and repolarization. BiophysJ. 2009; 97:2179-2190
35. Zlochiver S, Munoz V, Vikstrom K L, Taffet S M, Berenfeld O, Jalife J. Electrotonic myofibroblast-to-myocyte coupling increases propensity to reentrant arrhythmias in two-dimensional cardiac monolayers. Brophys J. 2008; 95:4469-4480
36. Morita N, Sovari A A, Xie Y, Fishbein M C, Mandel W J, Garfinkel A, Lin S F, Chen P S, Xie L H, Chen F, Qu Z, Weiss j N, Karagueuzian H S. Increased susceptibility of aged hearts to ventricular fibrillation during oxidative stress. Am J Physiol Heart Circ Physiol. 2009; 297:H1594-1605
37. Tanner H, Hindricks G, Kobza R, Dorszewski A, Schirdewahn P, Piorkowski C, Gerds-Li J H, Kottkamp H. Trigger activity more than three years after left atrial linear ablation without pulmonary vein isolation inpatients with atrial fibrillation. Journal of the American College of Cardiology. 2005; 46.338-343.
38. Daccarett M, McGann C J, Akoum N W, MacLeod R S, Marrouche N F. MRI of the left atrium: Predicting clinical outcomes inpatients with atrial fibrillation. Expert review of cardiovascular therapy. 2011; 9:105-111.

The above provides some examples according to particular embodiments of the current invention. The broad concepts of the current invention are not limited to only these particular examples. More generally, a method for identifying one or more ablation locations in a tissue region in an atrial fibrillation (AF) patient with atrial fibrosis according to an embodiment of the current invention includes receiving three-dimensional imaging data of a patient's atria, simulating at least one of electrophysiological or electromechanical activity of at least a portion of the patient's heart using the three-dimensional imaging data, and planning the patient-specific cardiac procedure based on the simulating. The cardiac procedure is for providing a preselected alteration of at least one of electrophysiological or electromechanical behavior of the patient's heart.

The three-dimensional imaging data can be MRI data as described in the examples above. However, the broad concepts of the current invention are not limited to that particular example. The three-dimensional imaging data can be can be at least one of magnetic resonance imaging (MRI), computed tomography (CT), positron emission tomography (PET), ultrasound, or nuclear tracer three-dimensional imaging data, for example. The method for identifying one or more ablation locations in an atrial tissue region can further include receiving additional patient-specific data in addition to the three-dimensional imaging data. For example, some embodiments can include receiving at least one of biopsy data, electrocardiogram data, recorded data from an implantable device (pace maker, defibrillator, etc.), or invasive electrical mapping data (e.g., endoscopic). The simulating can then use the additional patient-specific data for the simulation.

The simulating may include simulating at least one or both of electrophysiological or electromechanical activity of the atria or a portion of them. Simulating at least one of electrophysiological or electromechanical activity of the atria or a portion of them can include constructing a geometric model of the atria or a portion of them. The geometric model can include normal tissue regions and remodeled atrial tissue regions that are determined for the patient using the three-dimensional imaging data. The term "remodeled tissue" can include fibrosis, infarct scar, infarct border (gray) zone, or other disease-related structural, electrophysiological or contractile changes in the tissue. The simulating can further include estimating tissue fiber orientations in the geometric model of the atria. The estimation of fiber orientations can be done in a variety of ways. For example, the fiber orientations can be calculated using a Laplace-Dirichlet method to define the local axes at each spatial location in the atria (J. D. Bayer, R. Blake, G. Plank, Trayanova N, Novel rule based algorithm for assigning myocardial fiber orientation to computation heart models. *Ann Biomed Eng* (2012), the entire contents of which are incorporated herein by reference). Another approach could utilize pre-compiled data (i.e., atlas data), which can be mapped into the specific size and shape of the patient's heart (Image-Based Estimation of Ventricular Fiber Orientations for Personalized Modeling of Cardiac Electrophysiology, Vadakkumpadan F, Arevalo H, Ceritoglu C, Miller M, Trayanova N., IEEE Trans Med Imaging. 2012 Jan. 18 (the entire contents of which are incorporated herein by reference).

The geometric model of the tissue region may include at least a geometric model of right and left atria of the patient's heart. The remodeled tissue regions in this case can be segmented into a plurality of different regions based on the three-dimensional imaging data. The plurality of different regions can include fibrotic regions, scar tissue regions, normal tissues regions, and transition zones, for example, between normal and fibrotic tissue regions. The simulating in this case can be simulating electrophysiological activity of at least the right and left atria of the patient's heart.

The geometric model of the tissue region may include a geometric model of at least right and left atria of the patient's heart. In this embodiment, the remodeled tissue regions are fibrotic tissue regions. The simulating at least one of electrophysiological or electromechanical activity is simulating electrophysiological activity of at least the right and left atria of the patient's heart.

A computing device may perform certain functions in response to processor executing software instructions contained in a computer-readable medium, such as a memory. In alternative embodiments, hardwired circuitry may be used in place of or in combination with software instructions to implement features consistent with principles of the disclosure. Thus, implementations consistent with principles of the disclosure are not limited to any specific combination of hardware circuitry and software.

Exemplary embodiments may be embodied in many different ways as a software component. For example, it may be a stand-alone software package, a combination of software packages, or it may be a software package incorporated as a "tool" in a larger software product. It may be downloadable from a network, for example, a website, as a stand-alone product or as an add-in package for installation in an existing software application. It may also be available as a client-server software application, or as a web-enabled software application. It may also be embodied as a software package installed on a hardware device.

Numerous specific details have been set forth to provide a thorough understanding of the embodiments. It will be understood, however, that the embodiments may be practiced without these specific details. In other instances, well-known operations, components and circuits have not been described in detail so as not to obscure the embodiments. It can be appreciated that the specific structural and functional details are representative and do not necessarily limit the scope of the embodiments.

It is worthy to note that any reference to "one embodiment" or "an embodiment" means that a particular feature, structure, or characteristic described in connection with the embodiment is included in at least one embodiment. The appearances of the phrase "in one embodiment" in the specification are not necessarily all referring to the same embodiment.

Although some embodiments may be illustrated and described as comprising exemplary functional components or modules performing various operations, it can be appreciated that such components or modules may be implemented by one or more hardware components, software components, and/or combination thereof. The functional components and/or modules may be implemented, for example, by logic (e.g., instructions, data, and/or code) to be executed by a logic device (e.g., processor). Such logic may be stored internally or externally to a logic device on one or more types of computer-readable storage media.

Some embodiments may comprise an article of manufacture. An article of manufacture may comprise a storage medium to store logic. Examples of a storage medium may include one or more types of computer-readable storage media capable of storing electronic data, including volatile memory or non-volatile memory, removable or non-removable memory, erasable or non-erasable memory, writeable or re-writeable memory, and so forth. Examples of storage media include hard drives, disk drives, solid state drives, and any other tangible or non-transitory storage media.

It also is to be appreciated that the described embodiments illustrate exemplary implementations, and that the functional components and/or modules may be implemented in various other ways which are consistent with the described embodiments. Furthermore, the operations performed by such components or modules may be combined and/or separated for a given implementation and may be performed by a greater number or fewer number of components or modules.

Some of the figures may include a flow diagram. Although such figures may include a particular logic flow, it can be appreciated that the logic flow merely provides an exemplary implementation of the general functionality. Further, the logic flow does not necessarily have to be executed in the order presented unless otherwise indicated. In addition, the logic flow may be implemented by a hardware element, a software element executed by a processor, or any combination thereof.

The embodiments discussed in this specification are intended to explain concepts of the invention. However, the invention is not intended to be limited to the specific terminology selected and the particular examples described. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

What is claimed is:

1. A method for identifying one or more ablation locations in an atrial tissue region in an atrial fibrillation (AF) patient with atrial fibrosis, the method comprising:
   conducting simulation of AF using a patient-specific atrial model to identify AF-perpetrating regions;
   identifying from the AF-perpetrating regions one or more locations in the atria suitable for guided catheter ablation to make the atria non-inducible to AF; and
   conducting ablation on at least one of the identified one or more locations in the atria suitable for the guided catheter ablation,
   wherein the conducting the simulation comprises:
     identifying multiple groups of pacing locations according to pacing cycle length and proximity to at least one lesion in the patient-specific atrial model; and
     identifying at least one group from among the multiple groups that sustains AF during pacing.

2. The method of claim 1, wherein the AF-perpetrating regions comprise regions of tissue that contain organizing centers of persistent electrical rotors during the simulation.

3. The method of claim 2, wherein the persistent electrical rotors are re-circulating electrical waves in cardiac tissue.

4. The method of claim 1, wherein identifying from the AF-perpetrating regions one or more locations in the atria suitable for guided catheter ablation comprises simulating ablation of lesions within and around the AF-perpetrating regions to determine the size and shape of the lesion necessary to render the atria non-inducible to AF.

5. The method of claim 1, wherein conducting the simulation of AF using the patient-specific model further comprises determining whether pacing stimuli will degrade into reentrant activity.

6. The method of claim 1, wherein conducting the simulation of AF using the patient-specific atrial model further comprises using a dynamic pacing from different locations.

7. The method of claim 1, wherein conducting the simulation of AF using the patient-specific atrial model further comprises:

determining fibrotic lesions that lead to the breakup of pacing-induced wavefronts and degeneration of the wavefronts into reentrant waves that form AF rotors; and determining spatial location of the resulting AF rotors.

8. The method of claim 1, further comprising receiving additional patient-specific data that includes at least one of biopsy data, electrocardiogram data, recorded data from an implantable device, and invasive electrical mapping data, wherein conducting the simulation of AF using the patient-specific atrial model further comprises using the additional patient-specific data.

9. The method of claim 1, wherein conducting the simulation of AF using the patient-specific atrial model comprises simulating electrophysiological activity of at least the right atrium and the left atrium of the patient's heart.

10. The method of claim 1, wherein the patient-specific atrial model comprises fibrotic lesions with electrophysiological properties that are distinct from non-fibrotic regions.

11. The method of claim 1, wherein the patient-specific atrial model comprises:

a geometric model of at least the left atrium and the right atrium of the AF patient's heart, said geometric model including normal tissue regions and including remodeled tissue regions; and reference fiber orientations for the geometric model.

12. The method of claim 11, wherein the normal tissue regions and the remodeled tissue regions in the geometric model are determined for said patient using three-dimensional imaging data.

13. The method of claim 12, wherein said three-dimensional imaging data is at least one of magnetic resonance imaging (MRI) data, computed tomography (CT) data, positron emission tomography (PET) data, ultrasound data, or nuclear tracer three-dimensional imaging data.

* * * * *